United States Patent [19]

Lunkenheimer et al.

[11] Patent Number: 5,580,868

[45] Date of Patent: Dec. 3, 1996

[54] PYRIDYLOXY-ACRYLIC ACID ESTERS

[75] Inventors: Winfried Lunkenheimer, Wuppertal; Lutz Assmann, Eutin; Stefan Dutzmann, Hilden; Heinz-Wilhelm Dehne, Monheim; Gerd Hänssler, Leverkusen, all of Germany

[73] Assignee: Bayer Aktiengesellschaft, Leverkusen, Germany

[21] Appl. No.: 106,248

[22] Filed: Aug. 13, 1993

[30] Foreign Application Priority Data

Aug. 21, 1992 [DE] Germany .......................... 42 27 748.5

[51] Int. Cl.$^6$ .......................... A61K 31/54; A61K 31/44; C07D 213/78; C07D 413/00

[52] U.S. Cl. .................................. 514/222.5; 546/281.4; 546/282.4; 546/283.7; 546/284.1; 546/256; 546/257; 546/268.7; 546/269.4; 546/270.4; 546/271.1; 546/272.1; 546/275.4; 546/280.4; 546/283.4; 546/286; 546/268; 546/300; 546/301; 546/302; 546/271.4; 546/272.4; 546/274.1; 546/276.4; 514/229.2; 514/255.5; 514/241; 514/247; 514/252; 514/256; 514/344; 514/345; 514/351; 544/3; 544/8; 544/11; 544/66; 544/111; 544/124; 544/215; 544/224; 544/333; 544/405; 544/238

[58] Field of Search .................................. 546/301, 302, 546/300, 256, 257, 268, 269, 270, 271, 272, 275, 276, 277, 278, 280, 281, 283, 284, 286, 288; 544/3, 8, 11, 66, 111, 124, 215, 224, 333, 405, 238; 514/222.5, 229.2, 235.5, 241, 247, 252, 256, 344, 345, 351

[56] References Cited

FOREIGN PATENT DOCUMENTS

| | | |
|---|---|---|
| 0090353 | 10/1983 | European Pat. Off. . |
| 0212859 | 3/1987 | European Pat. Off. . |
| 0383117 | 8/1990 | European Pat. Off. . |
| 0535980 | 10/1992 | European Pat. Off. . |
| 1527638 | 12/1976 | United Kingdom . |
| 2238308 | 5/1991 | United Kingdom . |

OTHER PUBLICATIONS

Derwent Abstract, JO 2121–970, Agricultural Chemistry, Week 9025(1988).

JP(A)–C, Agricultural Chemistry, p. 2, week 9025, JP 02 121 970 (1988).

*Primary Examiner*—C. Warren Ivy
*Assistant Examiner*—Raymond Covington
*Attorney, Agent, or Firm*—Sprung Horn Kramer & Woods

[57] ABSTRACT

Novel pyridyloxy-acrylic acid esters of the formula $$\text{Ar} \underset{N}{\underset{\|}{\bigcirc}} \text{O} - \underset{\underset{O}{\|}}{C} \left( = CH - OCH_3 \right) - OCH_3 \quad (I)$$

in which

Ar represents optionally substituted aryl or represents optionally substituted heteroaryl, a process for preparing the novel compounds and their use as agents for combating pests.

Novel intermediates, processes for their preparation and their use for the synthesis of pyridyloxy-acrylic acid esters.

13 Claims, No Drawings

PYRIDYLOXY-ACRYLIC ACID ESTERS

The present invention relates to novel pyridyloxy-acrylic acid esters, a process for their preparation and their use as agents for combating pests.

It is already known that certain pyridyl-substituted acrylic acid esters possess fungicidal properties (cf. DE-OS (German Published Specification) 3 904 931). Thus, methyl 2-(6-phenyl-pyrid-2-yl-thio)-3-methoxy-acrylate and methyl 2-[N-methyl-N-(6-phenyl-pyrid-2-yl)-amino]-3-methoxy-acrylate, for example, may be employed for combating fungi. However, the activity of these compounds is not completely satisfactory in all areas of application, in particular when small quantities are used.

Novel pyridyloxy-acrylic acid esters have now been found of the formula

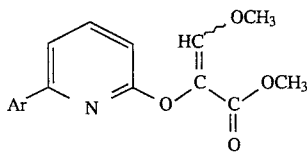

in which

Ar represents optionally substituted aryl or represents optionally substituted heteroaryl.

Depending on the position of the methoxy group on the C=C double bond, the compounds of the formula (I) may be present in the form of geometric isomers. The invention relates to both the isomeric mixtures and the individual isomers.

It has furthermore been found that pyridyloxy-acrylate acid esters of the formula (I) are obtained if acrylic acid derivatives of the formula

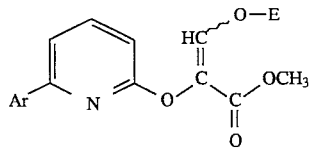

in which

E represents hydrogen or represents an alkali metal cation and

Ar has the abovementioned meaning are reacted with methylating agents of the formula

in which

A represents an electron-attracting leaving group, optionally in the presence of a diluent and optionally in the presence of an acid-binding agent as well as optionally in the presence of a catalyst.

Finally, it has been found that the novel pyridyloxy-acrylic acid esters of the formula (I) are very suitable for use as agents for combating pests. In particular, they can be employed against plant-damaging micro-organisms.

Surprisingly, the pyridyloxy-acrylic acid esters of the formula (I) according to the invention possess appreciably better efficacy towards plant-damaging microorganisms than methyl 1-(6-phenyl-pyrid-2-yl-thio)-2-methoxy-acrylate, methyl 1-[N-methyl-N-(6-phenyl-pyrid-2-yl)-amino]-2-methoxy-acrylate and methyl 1-[5-(4-chlorophenyl)-pyrid-3-yl-oxy]-2-methoxy-acrylate, which are previously known compounds that are closely related structurally and that act in the same direction.

The pyridyloxy-acrylic acid esters according to the invention are defined generally by the formula (I).

Ar preferably represents aryl having 6 to 10 carbon atoms, which can be substituted identically or differently once or more than once by halogen, hydroxyl, cyano, nitro, straight-chain or branched alkyl having 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl having 1 to 4 carbon atoms and/or halogenoalkyl having 1 to 4 carbon atoms and 1 to 9 halogen atoms, heterocyclyl having 3 to 7 ring members as well as 2 to 6 carbon atoms and 1 to 3 identical or different heteroatoms, such as nitrogen, oxygen and/or sulphur, which is optionally substituted identically or differently once to three times by halogen, alkyl having 1 to 4 carbon atoms and/or halogenoalkyl having 1 to 4 carbon atoms and 1 to 9 halogen atoms, and additionally by phenyl, phenoxy, benzyl, benzyloxy, phenylethyl or phenylethyloxy, where each of the 6 latter substituents can be substituted identically or differently once to three times in the phenyl moiety by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms, or Ar preferably represents optionally benzo-fused heteroaryl having 2 to 9 carbon atoms and 1 to 5 identical or different heteroatoms, such as nitrogen, oxygen and/or sulphur, where each of these radicals can be substituted once or more than once by halogen, hydroxyl, cyano, nitro, straight-chain or branched alkyl having 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl having 1 to 4 carbon atoms and/or halogenoalkyl having 1 to 4 carbon atoms and 1 to 9 halogen atoms, heterocyclyl having 3 to 7 ring members as well as 2 to 6 carbon atoms and 1 to 3 identical or different heteroatoms, such as nitrogen, oxygen and/or sulphur, which is optionally substituted identically or differently once to three times by halogen, alkyl having 1 to 4 carbon atoms and/or halogenoalkyl having 1 to 4 carbon atoms and 1 to 9 halogen atoms, and additionally by phenyl, phenoxy, benzyl, benzyloxy, phenylethyl or phenylethyloxy, where each of the 6 latter substituents can be substituted in the phenyl moiety identically or differently once to three times by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms.

Ar particularly preferably represents aryl having 6 to 10 carbon atoms, which can be substituted identically or differently once to five times by halogen, hydroxyl, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched alkylsulphinyl having 1 to 4 carbon atoms, straight-chain or branched alkyl sulphonyl having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched halogenoalkylsulphinyl having 1 to 4 carbon atoms and 1 to 9 identical or different halogen atoms, straight-chain or branched halogenoalkylsulphonyl having 1 to 4 carbon atoms and 1 to 9 identical or different halogen atoms, dialkylamino having 1 to 4 carbon atoms in each alkyl moiety, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, doubly linked alkylene having 1 to 3 carbon atoms, which is optionally substituted identically or differently once to three times by halogen, alkyl having 1 to 3 carbon atoms and/or halogenoalkyl having 1 to 3 carbon atoms and 1 to 7 identical or different halogen atoms, dioxyalkylene having 1 to 4 carbon atoms, which is optionally substituted identically or differently once to three times by halogen, alkyl having 1 to 3 carbon atoms and/or halogenoalkyl having 1 to 3 carbon atoms and 1 to 7 halogen atoms, cycloalkyl having 3 to 6 carbon atoms, which is optionally substituted identically or differently once to three times by halogen, alkyl having 1 to 3 carbon atoms and/or halogenoalkyl having 1 to 3 carbon atoms and 1 to 7 halogen atoms, saturated heterocyclyl having 5 to 7 ring members as well as 4 to 6 carbon atoms and 1 or 2 identical or different heteroatoms, such as nitrogen, oxygen and/or sulphur, which is optionally substituted identically or differently once to three times by halogen, alkyl having 1 to 3 carbon atoms and/or halogenoalkyl having 1 to 3 carbon atoms and 1 to 7 halogen atoms, and additionally by phenyl, phenoxy, benzyl, benzyloxy, phenylethyl or phenylethyloxy, where each of the 6 latter substituents can be substituted identically or differently once to three times in the phenyl moiety by halogen, alkyl having 1 to 3 carbon atoms, alkoxy having 1 to 3 carbon atoms, halogenoalkyl having 1 to 3 carbon atoms and 1 to 7 identical or different halogen atoms and/or by halogenoalkoxy having 1 to 3 carbon atoms and 1 to 7 identical or different halogen atoms, or Ar particularly preferably represents optionally benzofused heteroaryl having 2 to 9 carbon atoms and 1 to 3 identical or different heteroatoms, such as nitrogen, oxygen and/or sulphur, where each of these radicals can be substituted once to five times by halogen, hydroxyl, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched alkylsulphinyl having 1 to 4 carbon atoms, straight-chain or branched alkylsulphonyl having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched halogenoalkylsulphinyl having 1 to 4 carbon atoms and 1 to 9 identical or different halogen atoms, straight-chain or branched halogenoalkylsulphonyl having 1 to 4 carbon atoms and 1 to 9 identical or different halogen atoms, dialkylamino having 1 to 4 carbon atoms in each alkyl moiety, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, doubly linked alkylene having 1 to 4 carbon atoms, which is optionally substituted identically or differently once to three times by halogen, alkyl having 1 to 3 carbon atoms and/or halogenoalkyl having 1 to 3 carbon atoms and 1 to 7 identical or different halogen atoms, dioxyalkylene having 1 to 4 carbon atoms, which is optionally substituted identically or differently once to three times by halogen, alkyl having 1 to 3 carbon atoms and/or halogenoalkyl having 1 to 3 carbon atoms and 1 to 7 halogen atoms, cycloalkyl having 3 to 6 carbon atoms which is optionally substituted identically or differently once to three-times by halogen, alkyl having 1 to 3 carbon atoms and/or halogenoalkyl having 1 to 3 carbon atoms and 1 to 7 halogen atoms, heterocyclyl having 5 to 7 ring members as well as 4 to 6 carbon atoms and 1 or 2 identical or different heteroatoms, such as nitrogen, oxygen and/or sulphur, which is optionally substituted identically or differently once to three times by halogen, alkyl having 1 to 3 carbon atoms and/or halogenoalkyl having 1 to 3 carbon atoms and 1 to 7 halogen atoms, and additionally by phenyl, phenoxy, benzyl, benzyloxy, phenylethyl or phenylethyloxy, where each of the 6 latter substituents can be substituted identically or differently once to three times in the phenyl moiety by halogen, alkyl having 1 to 3 carbon atoms, alkoxy having 1 to 3 carbon atoms, halogenoalkyl having 1 to 3 carbon atoms and 1 to 7 identical or different halogen atoms and/or by halogenoalkoxy having 1 to 3 carbon atoms and 1 to 7 identical or different halogen atoms atoms.

Ar very particularly preferably represents phenyl or naphthyl, where each of these residues can be substituted identically or differently once to three times by fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, trifluoromethoxy, trifluoromethylthio, trifluoromethylsulphinyl, trifluoromethylsulphonyl, dimethylamino, diethylamino, methoxycarbonyl, ethoxycarbonyl, methoximinomethyl, methoximinoethyl, ethoximinomethyl, ethoximinoethyl, propane-1,3-diyl, butane-1,4-diyl, dioxymethylene, dioxyethylene, dioxypropylene, difluorodioxymethylene, tetrafluorodioxyethylene, cyclopropyl, cyclopentyl, cyclohexyl, 1-pyrrolidinyl, 1-piperidinyl, 1-perhydroazepinyl, 4-morpholinyl, phenyl, phenoxy, benzyl, benzyloxy or phenylethyloxy, where each of the 6 latter radicals can be substituted identically or differently once to three times in the phenyl moiety by fluorine, chlorine, bromine, methyl, ethyl, methoxy, ethoxy, trifluoromethyl and/or trifluoromethoxy, or Ar very particularly preferably represents furanyl, thienyl, pyrrolyl, oxazolyl, thiazolyl, isoxazolyl, isothiazolyl, pyrazolyl, imidazolyl, oxadiazolyl, thiadiazolyl, triazolyl, pyridyl, pyridazinyl, pyrimidinyl, pyrazinyl or triazinyl, where each of these radicals can be benzofused and can be substituted identically or differently once to three times by fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, trifluoromethoxy, trifluoromethylthio, trifluoromethylsulphinyl, trifluoromethylsulphonyl, dimethylamino, diethylamino, methoxycarbonyl, ethoxycarbonyl, methoximinomethyl, methoximinoethyl, ethoximinomethyl, ethoximinoethyl, propane-1,3-diyl, butane-1,4-diyl, dioxymethylene, dioxyethylene, dioxypropylene, difluorodioxymethylene, tetrafluorodioxyethylene, cyclopropyl, cyclopentyl, cyclohexyl, 1-pyrrolidinyl, 1-piperidinyl, 1-perhydroazepinyl, 4-morpholinyl, phenyl, phenoxy, benzyl, benzyloxy or phenylethyloxy, where each of the 6 latter radicals can be substituted identically of differently once to three times in the phenyl moiety by fluorine, chlorine, bromine, methyl, ethyl, methoxy, ethoxy, trifluoromethyl and/or trifluoromethoxy.

The pyridyloxy-acrylic acid esters listed in the following table may be mentioned as examples of compounds according to the invention.

TABLE 1

Ar—pyridine—O—C(=CHOCH$_3$)—C(=O)OCH$_3$ (I)

| Ar | Ar | Ar |
|---|---|---|
| C$_6$H$_5$—C$_6$H$_4$— | Br—C$_6$H$_4$— | Br (3-Br-C$_6$H$_4$)— |
| 3,4-Cl$_2$-C$_6$H$_3$— | 3,4-(H$_3$C)$_2$-C$_6$H$_3$— | 3,4-(H$_3$CO)$_2$-C$_6$H$_3$— |
| t-C$_4$H$_9$—C$_6$H$_4$— | (CH$_3$)$_2$N—C$_6$H$_4$— | i-C$_3$H$_7$—O—C$_6$H$_4$— |

TABLE 1-continued
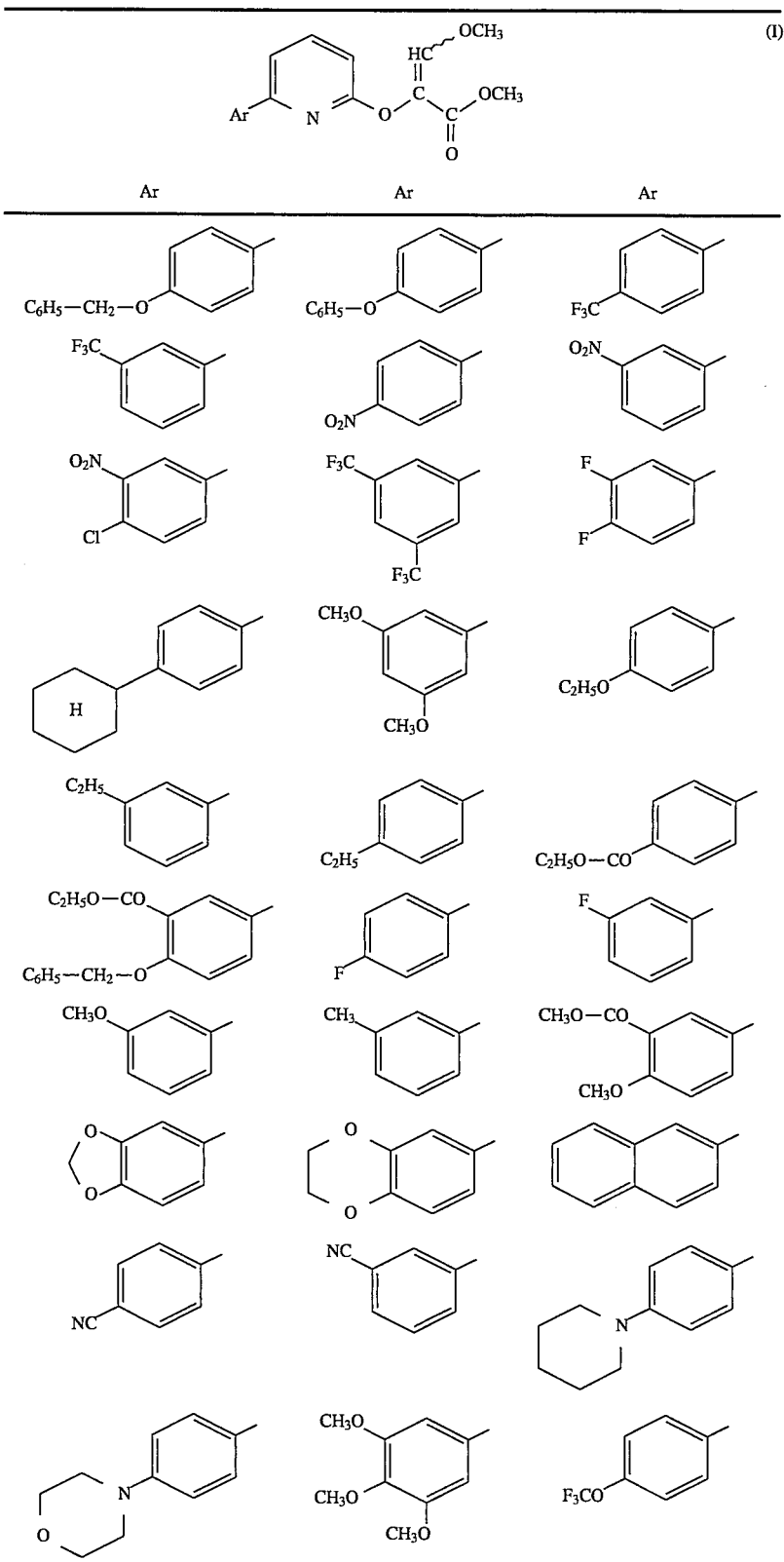

TABLE 1-continued
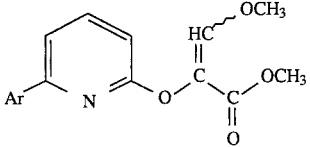
If methyl 2-[6-(4-chlorophenyl)-pyrid-2-yloxy]-1-hydroxy-methylene-acrylate and dimethyl sulphate are used as starting compounds, the course of the reaction of the process according to the invention can be represented by the following formula diagram:
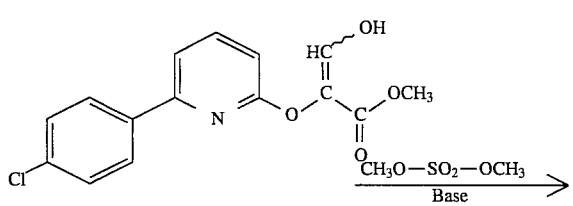

-continued

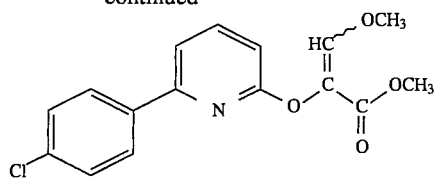

The acrylic acid derivatives required as starting compounds for carrying out the process according to the invention are generally defined by the formula (II). In this formula (II), Ar preferably represents those residues which have already been mentioned as preferred for these substituents in connection with the description of the compounds of the formula (I) according to the invention.

E preferably represents hydrogen or represents a sodium or potassium cation.

The acrylic acid derivatives of the formula (II) have not previously been known. They can be prepared by reacting 6-aryl-2-pyridones of the formula

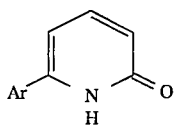 (IV)

in which

Ar has the abovementioned meaning,
with halogenoacetic acid esters of the formula

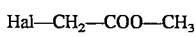 (V)

Hal—CH$_2$—COO—CH$_3$ in which

Hal represents halogen,
optionally in the presence of a diluent, and optionally in the presence of an acid-binding agent, and then reacting the pyridyloxyacetic acid esters obtainable in this way, of the formula (VI)

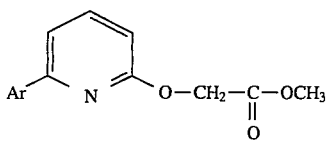 (VI)

in which

Ar has the abovementioned meaning,
in a subsequent second stage either
a) with alkyl formates of the formula

 (VII)

H—COOR in which

R represents alkyl,
optionally in the presence of a diluent, or optionally in the presence of an acid-binding agent,
or
b) with dialkylformamide derivatives of the formula

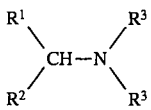 (VIII)

in which

R$^1$ and R$^2$ independently of each other represent alkoxy or dialkylamino and R$^3$ represents alkyl, optionally in the presence of a diluent, and then subsequently reacting the 2-dialkylaminoacrylic acid derivatives obtainable in this way, of the formula

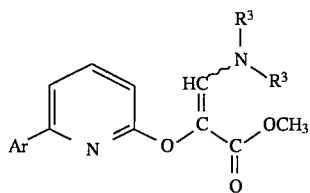 (IX)

in which

R$^3$ and Ar have the abovementioned meaning,
with water, optionally in the presence of an acid,
and converting the resulting acrylic acid derivatives, in which E represents hydrogen, into the alkali metal salts, optionally using alkali metal hydroxide.

The 6-aryl-2-pyridones of the formula (IV) which are required as starting compounds in the preparation of acrylic acid derivatives of the formula (II) according to the above process, are known or can be prepared by processes which are known in principle (cf. e.g. Chem. Ber. 90, 711 [1957]; Ber. dtsch. Chem. Ges. 55, 359 [1922]; Organic Syntheses Coll. Vol. III, 305 [1955]; Angew. Chem. 88, 261, [1976]; Helv. Chim. Acta 24, 233E [1941]).

The halogenoacetic acid esters which are required as reaction components in the above process for preparing acrylic acid derivatives of the formula (II) are generally defined by the formula (V). In this formula, Hal preferably represents chlorine, bromine or iodine. The halogenoacetic acid esters of the formula (V) are known.

The alkyl formates which are additionally required as reaction components are generally defined by the formula (VII). In this formula, R preferably represents methyl or ethyl. The alkyl formates of the formula (VII) are known.

The dialkylformamide derivatives which are also required as reaction components are generally defined by the formula (VIII). In this formula, R$^1$ and R$^2$ preferably represent, independently of each other, methoxy, ethoxy, dimethylamino or diethylamino. R$^3$ preferably represents methyl or ethyl. The dialkylformamide derivatives of the formula (VIII) are known.

The pyridyloxyacetic acid esters of the formula (VI) and 2-dialkylamino-acrylic acid derivatives of the formula (IX), which appear as intermediates in the above process for preparing acrylic acid derivatives of the formula (II), have not previously been known.

All inert organic solvents which are customary for reactions of this nature are suitable as diluents in the reaction of 6-aryl-2-pyridones of the formula (IV) with halogenoacetic acid esters of the formula (V). Ethers, such as 1,2-dimethoxyethane, are preferably used.

All customary strong bases are suitable as acid-binding agents in the reaction of 6-aryl-2-pyridones of the formula (IV) with halogenoacetic acid esters of the formula (V). Hydrides, such as sodium hydride, are preferably used.

The reaction temperatures in the above reaction of 6-aryl-2-pyridones of the formula (IV) with halogenoacetic acid esters of the formula (V) may be varied within a relatively wide range. In general, temperatures between 50° C. and 150° C. are employed.

All inert organic solvents which are customary for reactions of this nature are suitable as diluents in the reaction of pyridyloxyacetic acid esters of the formula (VI) with alkyl formates of the formula (VII). Acid amides, such as dimethylformamide, are preferably used.

All customary strong bases are suitable as acid-binding agents in the reaction of pyridyloxyacetic acid esters of the formula (VI) with alkyl formates of the formula (VII). Hydrides, such as sodium hydride, are preferably used.

The reaction temperatures in the reaction of pyridyloxyacetic acid esters of the formula (VI) with alkyl formates of the formula (VII) may also be varied within a relatively wide range. In general, temperatures between −20° C. and +50° C. are employed.

All inert organic solvents which are customary for reactions of this nature are suitable as solvents in the reaction of pyridyloxyacetic acid esters of the formula (VI) with dialkylformamide derivatives of the formula (VIII). Ethers, such as 1,2-dimethoxyethane, are preferably used.

The reaction temperatures in the reaction of pyridyloxyacetic acid esters of the formula (VI) with dialkylformamide derivatives of the formula (VIII) may likewise be varied within a relatively wide range. In general, temperatures between −20° C. and +150° C. are employed.

All customary strong inorganic and organic acids are suitable as acids in the reaction of 2-dialkylaminoacrylic acid derivatives of the formula (IX) with water. Aqueous hydrohalic acids, in particular hydrochloric acid, are preferably used.

The reaction temperatures in the reaction of 2-dialkylaminoacrylic acid derivatives of the formula (IX) with water may also be varied within a relatively wide range. In general, temperatures between 0 ° C. and +120 ° C. are employed.

The reactions for preparing acrylic acid derivatives of the formula (II) according to the above process are generally carried out under atmospheric pressure. However, it is also possible to use elevated or reduced pressure.

For the rest, the reaction components in the above process for preparing acrylic acid derivatives of the formula (II) are employed in approximately equimolar quantities. However, it is also possible to use one or other component in excess. Working up takes place on each occasion according to customary methods.

Those acrylic acid derivatives of the formula (II) in which E represents hydrogen may be converted into the corresponding alkali metal salts using alkali metal hydroxides, such as sodium hydroxide or potassium hydroxide.

The methylating agents which are required as reaction components in carrying out the process according to the invention are generally defined by the formula (III). In this formula, A preferably represents halogen, optionally substituted alkylsulphonyloxy, optionally substituted alkoxysulphonyloxy or optionally substituted arysulphonyloxy. A particularly preferably represents chlorine, bromine, iodine, methylsulphonyloxy, trifluoromethylsulphonyloxy, methoxysulphonyloxy, ethoxysulphonyloxy or p-tolylsulphonyloxy.

The methylating agents of the formula (III) are generally known compounds of organic chemistry.

Inert organic solvents are suitable diluents for carrying out the process according to the invention. Those which are preferably used are aliphatic, alicyclic or aromatic, optionally halogenated, hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide or sulphoxides, such as dimethyl sulphoxide.

The process according to the invention may optionally be carried out in a two-phase system, such as, for example, water/toluene or water/dichloromethane, optionally in the presence of a suitable phase transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}$/$C_{15}$-alkylammonium chloride, trimethyl-$C_{13}$/$C_{15}$-alkylammonium bromide, dibenzyl-dimethyl-ammoniummethyl sulphate, dimethyl-$C_{12}$/$C_{14}$-alkylbenzylammonium chloride, dimethyl-$C_{12}$/$C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxy-ethoxy)-ethyl]-amine.

The process according to the invention is preferably carried out in the presence of an acid-binding agent. All customary inorganic or organic bases are suitable as such agents. Those which are preferably used are hydrides, hydroxides, amides, alcoholates, acetates, carbonates or hydrogen carbonates of alkaline earth metals or alkali metals, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate as well as tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

In carrying out the process according to the invention, the reaction temperatures may be varied within a relatively wide range. In general, temperatures between −30° C. and +120° C. are employed, preferably temperatures between −20° C. and +60° C.

The process according to the invention is usually carried out under atmospheric pressure. However, it is also possible to use elevated or reduced pressure.

For carrying out the process according to the invention, 1.0 to 10.0 mol, preferably 1.0 to 5.0 mol, of methylating agent of the formula (III) and optionally 1.0 to 5.0 mol, preferably 1.0 to 2.5 mol, of acid-binding agent are generally employed per mol of acrylic acid derivative of the formula (II). In this context, it is possible, for carrying out the process according to the invention, to prepare the acrylic acid derivatives of the formula (II), which are required as starting compounds, in a prior reaction directly in the reaction vessel, and subsequently to continue the reaction according to the invention without any isolation (one pot variant). Implementation of the reaction, working up and isolation of the reaction products, takes place according to known processes (cf. in this context, for example, DE-OS (German Published Specification) 39 04 931 or the preparation examples).

Purification of the end products of the formula (I) is effected using customary processes, for example by column chromatography or by recrystallisation.

Characterisation is effected using the melting point or, in the case of non-crystallising compounds, using the refractive index or proton nuclear magnetic resonance spectroscopy ($^1$H-NMR).

The active compounds according to the invention possess powerful microbicidal activity and may be employed in practice for combating unwanted microorganisms. The active compounds are suitable for use in plant protection as agents for combating pests, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*; Plasmopara species, such as, for example, *Plasmopara viticola*;
Peronospora species, such as, for example, *Peronospora pisi* or *Peronospora brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *Pyrenophora graminea* (conidia form: Drechslera, synonym: Helminthosporium);
Cochliobolus species, such as, for example, *Cochliobolus sativus* (conidia form: Drechslera, synonym: Helminthosporium);
Uromyces species, such as, for example, *Uromyces appendiculatus*;
Puccinia species, such as, for example, *Puccinia recondita*;
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae* and
Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this context, the active compounds according to the invention may be employed particularly successfully for combating cereal diseases, for example against the causative agent of powdery mildew on wheat or barley (*Erysiphe graminis*) or against the causative agent of net blotch of barley (*Pyrenophora teres*) or against the causative agent of spot blotch on barley or wheat (*Cochliobolus sativus*) or against the causative agent of glume blotch of wheat (*Leptosphaeria nodorum*) or against causative agents of fusarioses (*Fusarium species*) or for combating diseases in fruit and vegetable cultivation, for example against the causative agent of tomato blight (*Phytophthora infestans*) or against the causative agent of apple scab (*Ventura inaequalis*) or against types of powdery mildew in fruit and vegetable cultivation or for combating rice diseases, for example against the causative agent of rice blast disease (*Pyricularia oryzae*) or against the causative agent of rice stem blight (*Pellicularia sasakii*). Besides this, the active compounds according to the invention possess broad in-vitro activity.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and use of the active compounds according to the invention is evident from the following examples.

PREPARATION EXAMPLES

EXAMPLE 1

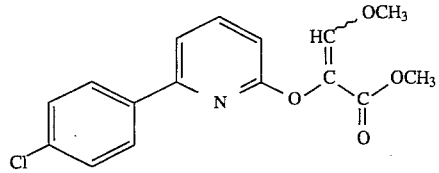

(I-1)

A solution of 2.9 g (0.01 mol) of methyl 2-[6-(4-chlorophenyl)-pyrid-2-yloxy]-acetate in 15 g (0.25 mol) of methyl formate is added dropwise within 30 minutes while stirring at 5° C. to 10° C. to a suspension of 0.6 g (0.02 mol) of 80% sodium hydride in 30 ml of absolute dimethylformamide, and after completed addition the mixture is stirred at room temperature for 4 hours. For the working up, 15 ml of saturated aqueous sodium hydrogen carbonate solution are added while cooling with ice and the mixture is extracted three times with 20 ml of ether on each occasion, and the aqueous phase is then acidified with dilute hydrochloric acid and extracted three times with 20 ml of ethyl acetate on each occasion. The combined organic phases are dried and concentrated under reduced pressure. The remaining oil is dissolved in 30 ml of absolute dimethylformamide, and 4 g (0,011 mol) of pulverised potassium carbonate are added to the solution, which is stirred at room temperature for 15 minutes, after which 1.3 g (0,011 mol) of dimethyl sulphate are added dropwise while stirring. Next, the mixture is stirred at room temperature for 19 hours, 20 ml of saturated aqueous sodium carbonate solution are added, the mixture is extracted three times with ethyl acetate, and the combined organic phases are dried over sodium sulphate and concentrated under reduced pressure and the residue is purified by chromatography on silica gel (eluent: dichloromethane).

1.2 g (35% of theory) of methyl 2-[6-(4-chlorophenyl)-pyrid-2-yloxy]-3-methoxy-acrylate are obtained with a melting point of 50°–54° C.

The pyridyloxy-acrylic acid esters of the formula (I) listed in Table 2 below are obtained in a corresponding manner and in accordance with the general preparation instructions:

TABLE 2

| Example number | Compound No. | Ar | Physical properties |
|---|---|---|---|
| 2 | (I-2) | phenyl | m.p. 66–68° C. |
| 3 | (I-3) | 3-chlorophenyl | m.p. 84–86° C. |
| 4 | (I-4) | 4-methylphenyl | m.p. 76–78° C. |
| 5 | (I-5) | 4-methoxyphenyl | m.p. 48–50° C. |
| 6 | (I-6) | 4,5-dichloro-2-methylphenyl | m.p. 132–134° C. |

PREPARATION OF THE STARTING COMPOUNDS

EXAMPLE 7

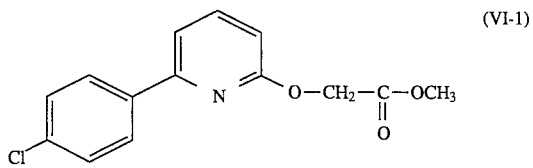

(VI-1)

A solution of 17 g (0.11 mol) of methyl bromoacetate in 25 ml of 1,2-dimethoxyethane is added dropwise while stirring at reflux temperature to a mixture of 3.75 g (0.125 mol) of 80% sodium hydride, 150 ml of 1,2-dimethoxyethane and 20.8 g (0.1 mol) of 6-(4-chlorophenyl)-2-pyridone and the mixture is subsequently heated at reflux temperature for a further 4 hours. For working up, the solvent is distilled off and the residue is partitioned between 100 ml of ethyl acetate and 30 ml of water. The organic phase is separated off, washed with water, dried over sodium sulphate and concentrated under reduced pressure. The residue is purified by chromatography on silica gel (eluent: dichloromethane).

20.3 g (72% of theory) of methyl 2-[6-(4-chlorophenyl)-pyrid-2-yloxy]-acetate are obtained with a melting point of 60°–63° C.

The pyridyloxyacetic acid esters of the formula (VI) listed in Table 3 below are obtained in a corresponding manner and in accordance with the general preparation instructions.

TABLE 3

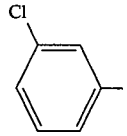

(VI)

| Example number | Compound No. | Ar | Physical properties |
|---|---|---|---|
| 8 | VI-2 | C$_6$H$_5$ | m.p. 58–60° C. |
| 9 | VI-3 | 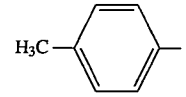 | m.p. 55–57° C. |
| 10 | VI-4 | 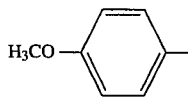 | m.p. 42–45° C. |
| 11 | VI-5 | 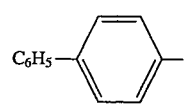 | m.p. 87–88° C. |
| 12 | VI-6 | 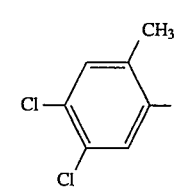 | m.p. 135–136° C. |
| 13 | VI-7 | 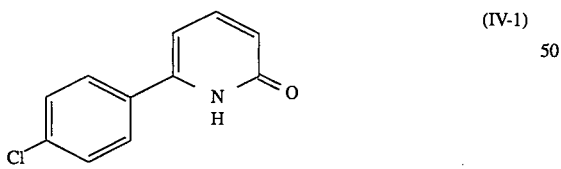 | m.p. 77–79° C. |

EXAMPLE 14

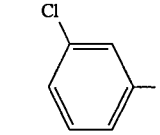

(IV-1)

74.2 g (0.35 mol) of 1-(4-chlorophenyl)-3-dimethylamino-1-propanone (preparation, cf. Ber. dtsch. Chem. Ges. 55, 359 [1922]) and 60.2 g (0.35 mol) of 1-carbamoylmethylpyridinium chloride (preparation, cf. Helv. Chim. Acta 24, 233E [1941]) in 1.4 l of methanol are heated at reflux temperature for 3 hours, with the dimethylamine which is liberated being simultaneously driven off with a stream of nitrogen which is passed through the reaction mixture. For working up, the solvent is distilled off, the residue is mixed with 700 ml of formamide and 70 ml of glacial acetic acid and the mixture is heated at 190° C. (bath temperature) for 2 hours. For the working up, 650 ml of water are added to the cooled reaction mixture which is then extracted five times with 300 ml of chloroform on each occasion. The combined organic phases are dried and concentrated under reduced pressure. The residue is caused to crystallise by stirring with a mixture of 300 ml of ether and 30 ml of ethanol, filtered off with suction and dried.

23.2 g (32% of theory) of 6-(4-chlorophenyl)-2-pyridone are obtained with a melting point of 200°–203° C.

The 6-aryl-2-pyridones of the formula (IV) listed in Table 4 below are obtained in a corresponding manner and in accordance with the general preparation instructions.

TABLE 4

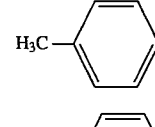

(IV)

| Example number | Compound No. | Ar | Physical properties |
|---|---|---|---|
| 15 | IV-2 | C$_6$H$_5$ | m.p. 190–192° C. |
| 16 | IV-3 | 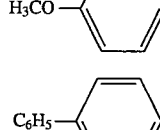 | m.p. 155–158° C. |
| 17 | IV-4 | 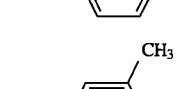 | m.p. 174–176° C. |
| 18 | IV-5 | 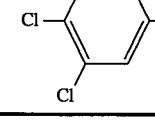 | m.p. 195–196° C. |
| 19 | IV-6 | 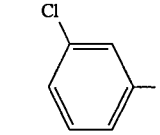 | m.p. >240° C. |
| 20 | IV-7 | 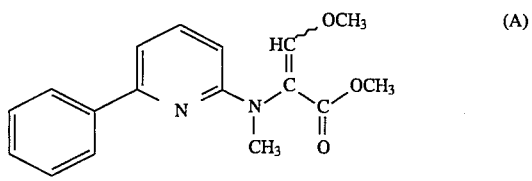 | m.p. 206–208° C. |

APPLICATION EXAMPLES

In the following application examples, the compounds listed below were employed as comparison substances:

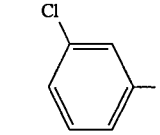

(A)

Methyl 2-[N-methyl-N-(6-phenyl-pyrid-2-yl)-amino]-3-methoxy-acrylate

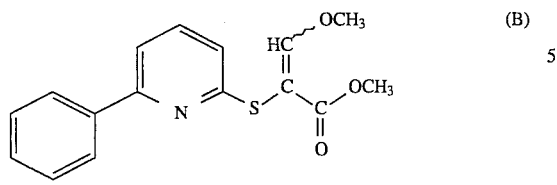

(B)

Methyl 2-(6-phenyl-pyrid-2-yl-thio)-3-methoxy-acrylate

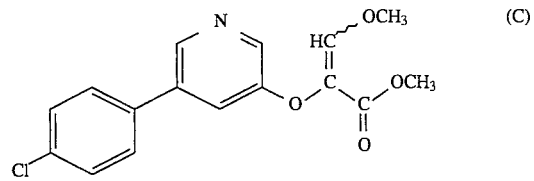

(C)

Methyl 2-[5-(4-chlorophenyl)-pyrid-3-yl-oxy]-3-methoxyacrylate (all known from DE-OS (German Published Specification) 39 04 931)

EXAMPLE A

Venturia test (apple)/protective
  Solvent: 4.7 parts by weight of acetone
  Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compounds according to the invention listed in Examples 1 to 6 exhibit, at a concentration of active compound in the spray liquor of 10 ppm, an efficiency of over 80%, while the comparison substance (C) only exhibits an efficiency of about 30%.

EXAMPLE B

*Leptosphaeria nodorum* test (wheat)/protective
  Solvent: 100 parts by weight of dimethylformamide
  Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, the compounds according to the invention listed in Examples 1 and 4 exhibit, at a concentration of active compound in the spray liquor of 250 ppm, an efficiency of 100%, while the comparison substance (C) does not exhibit any activity.

EXAMPLE C

Erysiphe test (barley)/protective
  Solvent: 100 parts by weight of dimethylformamide
  Emulsifier: 0.25 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C and a relative atmospheric humidity of about 80%, in order to promote the development of mildew pustules.

Evaluation is carried out 7 days after the inoculation.

In this test, the compounds according to the invention listed in Examples 1 to 3 exhibit, at a concentration of active compound in the spray liquor of 250 ppm, an efficiency of more than 80%, while the comparison substances (A) and (B) exhibit an efficiency of 25%.

EXAMPLE D

Phytophthora test (tomato)/protective
  Solvent: 4.7 parts by weight of acetone
  Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are then placed in an incubation cabin at 20° C. and at a relative atmospheric-humidity of about 100%.

Evaluation is carried out 3 days after the inoculation.

In this test, the compounds according to the invention listed in Examples 1 to 4 exhibit, at a concentration of active compound in the spray liquor of 10 ppm, an efficiency of more than 80%, while the comparison substances (B) and (A) exhibit no effect or only an efficiency of 50%.

EXAMPLE E

Pyricularia test (rice)/protective
  Solvent: 12.5 parts by weight of acetone
  Emulsifier: 0.3 part by weight of alkyl-aryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*.

The plants are then placed in a greenhouse at 100% relative atmospheric humidity and 25° C.

Evaluation of the disease infestation is carried out 4 days after the inoculation.

In this test, the compounds according to the invention listed in Examples 1 to 5 exhibit, at a concentration of active compound in the spray liquor of 0.025%, an efficiency of 100%, while the comparison substance (C) only exhibits an efficiency of 30%.

EXAMPLE F

Pellicularia test (rice)

Solvent: 12.5 parts by weight of acetone

Emulsifier: 0.3 part by weight of alkyl-aryl polyglycol ether

To produce a suitable preparation of active compound, 1 part by weight of active compound is mixed with the stated amounts of solvent, and the concentrate is diluted with water and the stated amount of emulsifier to the desired concentration.

To test for activity, young rice plants in the 3 to 4 leaf stage are sprayed with the preparation of active compound until dripping wet. The plants remain in a greenhouse until they have dried off. The plants are then inoculated with *Pellicularia sasakii* and are placed in a greenhouse at 25° C. and 100% relative atmospheric humidity.

The evaluation of the disease infestation is carried out 5 to 8 days after the inoculation.

In this test, the compounds according to the invention listed in Examples 2, 4 and 5 exhibit, at a concentration of active compound in the spray liquor of 0.025%, an efficiency of over 70% and more, while the comparison substance (C) exhibits an efficiency of 30%.

We claim:

1. A pyridyloxy-acrylic acid ester of the formula 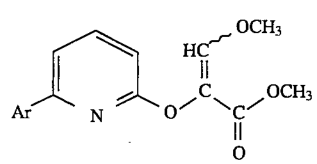 in which

Ar is substituted aryl which is substituted identically or different once or more then once and the substituents are halogen, hydroxyl, cyano, nitro, straight-chain or branched alkyl having 1 to 6 carbon atoms, straight-chain or branched alkoxy having i to 6 carbon atoms, straight-chain or branched alkylthio having 1 to 6 carbon atoms, straight-chain or branched alkylsulphinyl having 1 to 6 carbon atoms, straight-chain or branched alkysulphonyl having 1 to 6 carbon atoms, straight chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl having 1 to 4 carbon atoms and/or halogenoalkyl having 1 to 4 carbon atoms and 1 to 9 halogen atoms, heterocyclyl having 3 to 7 ring members, 2 to 6 carbon atoms and 1 to 3 identical or different heteroatoms, wherein the heteroatoms are nitrogen, oxygen and/or sulphur, which is optionally substituted identically or differently once to three times by halogen, alkyl having 1 to 4 carbon atoms and/or halogenoalkyl having 1 to 4 carbon atoms and 1 to 9 halogen atoms, and additionally by phenyl, phenoxy, benzyl, benzyloxy, phenylethyl or phenylethyloxy, where each of the 6 latter substituents are optionally substituted identically or differently once to three times in the phenyl moiety by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms, or Ar represents an optionally benzo-fused heteroaryl having 2 to 9 carbon atoms and 1 to 5 identical or different heteroatoms and 1 to 5 identical or different heteroatoms, where each of these radicals is substituted once or more than once by halogen, hydroxyl, cyano, nitro, straight-chain or branched alkyl 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl having 1 to 4 carbon atoms and/or halogenoalkyl having 1 to 4 carbon atoms and 1 to 9 halogen atoms, heterocyclyl having 3 to 7 ring members, 2 to 6 carbon atoms and 1 to 3 identical or different heteroatoms wherein the heteroatoms are oxygen and/or sulphur, which is optionally substituted identically or differently once to three times by halogen, alkyl having 1 to 4 carbon atoms and/or halogenoalkyl having 1 to 4 carbon atoms and 1 to 9 halogen atoms, and additionally by phenyl, phenoxy, benzyl, benzyloxy, phenylethyl or phenylethyloxy, where each of the 6 latter substituents are optionally substituted in the phenyl moiety identically or differently once to three times by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms.

2. A compound according to claim 1, wherein

Ar is phenyl, furanyl, thienyl, pyrrolyl, oxazolyl, thiazolyl, isoxazolyl, isothiazolyl, pyrazolyl, imidazolyl, oxadiazinyl, thiadiazolyl, triazolyl, pyridyl, pyridazinyl, pyrimidinyl, pyrazinyl or triazinyl.

3. A compound according to claim 2, wherein the substituent is halogen, alkyl, or phenoxy.

4. A compound according to claim 2 wherein the substituent is chlorine or methyl.

5. A compound according to claim 2, wherein the compound is

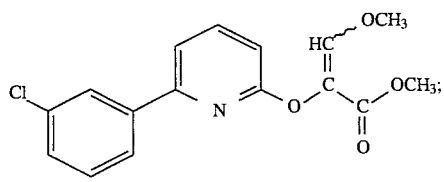

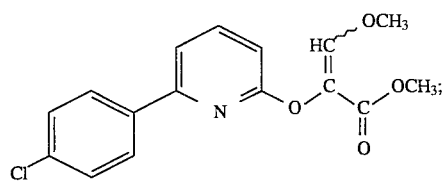

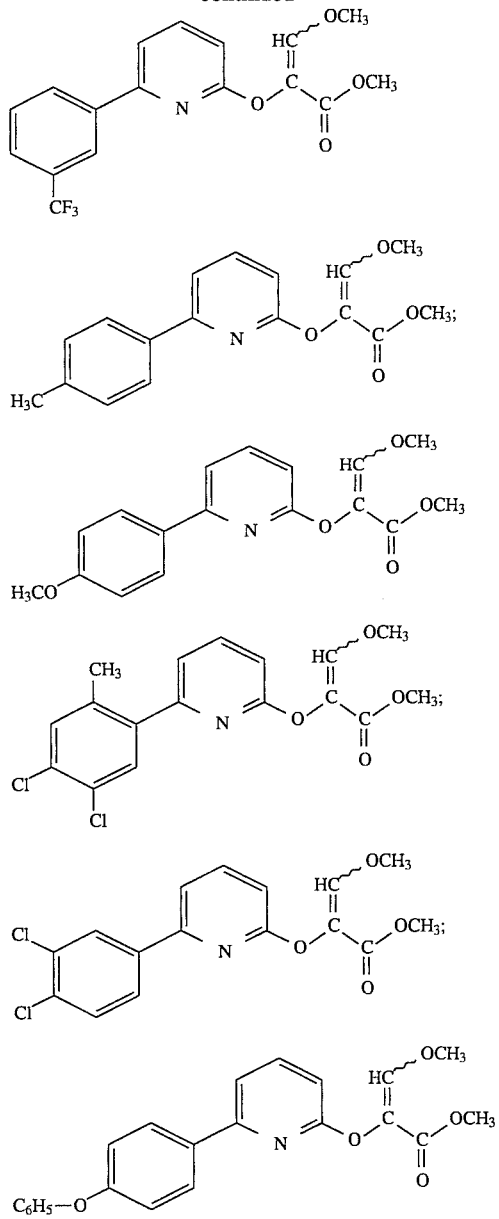

6. A composition for combatting pests comprising an effective amount of a compound according to claim 1 and an inert carrier.

7. A method for combatting pests which comprises applying a compound according to claim 1 to said pest or to its environment.

8. An acrylic acid derivative to the formula

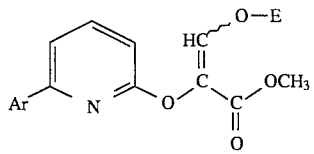

wherein

Ar is substituted aryl which is substituted identically or different once or more then once and the substituents are halogen, hydroxyl, cyano, nitro, straight-chain or branched alkyl having 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkysulphonyl having 1 to 6 carbon atoms, straight chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl having 1 to 4 carbon atoms and/or halogenoalkyl having 1 to 4 carbon atoms and 1 to 9 halogen atoms, heterocyclyl having 3 to 7 ring members, 2 to 6 carbon atoms and 1 to 3 identical or different heteroatoms, wherein the heteroatoms are nitrogen, oxygen and/or sulphur, which is optionally substituted identically or differently once to three times by halogen, alkyl having 1 to 4 carbon atoms and/or halogenoalkyl having 1 to 4 carbon atoms and 1 to 9 halogen atoms, and additionally by phenyl phenoxy, benzyl, benzyloxy, phenylethyl or phenylethyloxy, where each of the 6 latter substituents are optionally substituted identically or differently once to three times in the phenyl moiety by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms, or Ar represents an optionally benzo-fused heteroaryl having 2 to 9 carbon atoms and 1 to 5 identical or different heteroatoms and i to 5 identical or different heteroatoms, where each of these radicals is substituted once or more than once by halogen, hydroxyl, cyano, nitro, straight-chain or branched alkyl 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl having 1 to 4 carbon atoms and/or halogenoalkyl having 1 to 4 carbon atoms and 1 to 9 halogen atoms, heterocyclyl having 3 to 7 ring members, 2 to 6 carbon atoms and 1 to 3 identical or different heteroatoms wherein the heteroatoms are oxygen and/or sulphur, which is optionally substituted identically or differently once to three times by, halogen, alkyl having 1 to 4 carbon atoms and/or halogenoalkyl having 1 to 4 carbon atoms and 1 to 9 halogen atoms, and additionally by phenyl, phenoxy, benzyl, benzyloxy, phenylethyl or phenylethyloxy, where each of the 6 latter substituents are optionally substituted in the phenyl moiety identically or differently once to three times by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms.

and

E represents hydrogen or an alkali metal cation.

9. The compound according to claim 8, wherein the substituent on Ar is halogen, alkyl or phenoxy.

10. A pyridyloxyacetic acid ester of the formula

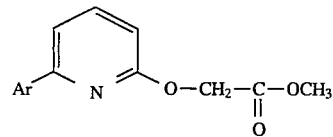

wherein

Ar is substituted aryl which is substituted identically or different once or more then once and the substituents are halogen, hydroxyl, cyano, nitro, straight-chain or branched alkyl having 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkysulphonyl having 1 to 6 carbon atoms, straight chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl having 1 to 4 carbon atoms and/or halogenoalkyl having 1 to 4 carbon atoms and 1 to 9 halogen atoms, heterocyclyl having 3 to 7 ring members, 2 to 6 carbon atoms and 1 to 3 identical or different heteroatoms, wherein the heteroatoms are nitrogen, oxygen and/or sulphur, which is optionally substituted identically or differently once to three times by halogen, alkyl having 1 to 4 carbon atoms and/or halogenoalkyl having 1 to 4 carbon atoms and 1 to 9 halogen atoms, and additionally by phenyl, phenoxy, benzyl, benzyloxy, phenylethyl or phenylethyloxy, where each of the 6 latter substituents are optionally substituted identically or differently once to three times in the phenyl moiety by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms, or Ar represents an optionally benzo-fused heteroaryl having 2 to 9 carbon atoms and 1 to 5 identical or different heteroatoms and 1 to 5 identical or different heteroatoms, where each of these radicals is substituted once or more than once by halogen, hydroxyl, cyano, nitro, straight-chain or branched alkyl 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms-and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl having 1 to 4 carbon atoms and/or halogenoalkyl having 1 to 4 carbon atoms and 1 to 9 halogen atoms, heterocyclyl having 3 to 7 ring members, 2 to 6 carbon atoms and 1 to 3 identical or different heteroatoms wherein the heteroatoms are oxygen and/or sulphur, which is optionally substituted identically or differently once to three times by halogen, alkyl having 1 to 4 carbon atoms and/or halogenoalkyl having 1 to 4 carbon atoms and 1 to 9 halogen atoms, and additionally by phenyl, phenoxy, benzyl, benzyloxy, phenylethyl or phenylethyloxy, where each of the 6 latter substituents are optionally substituted in the phenyl moiety identically or differently once to three times by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms.

11. The compound according to claim 10 wherein the substituent on Ar is halogen, alkyl or phenoxy.

12. A 2-dialkylamino acrylic acid derivative of the formula

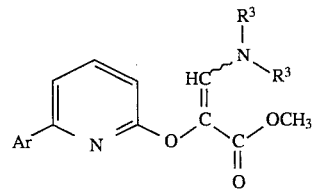

wherein

Ar is substituted aryl which is substituted identically or different once or more then once and the substituents are halogen, hydroxyl, cyano, nitro, straight-chain or branched alkyl having 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight,chain or branched alkysulphonyl having 1 to 6 carbon atoms, straight chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl 4 carbon atoms and/or halogenoalkyl having 1 to 4 carbon atoms and 1 to 9 halogen atoms, heterocyclyl having 3 to 7 ring members, 2 to 6 carbon atoms and 1 to 3 identical or different heteroatoms, wherein the heteroatoms are nitrogen, oxygen and/or sulphur, which is optionally substituted identically or differently once to three times by halogen, alkyl having 1 to 4 carbon atoms and/or halogenoalkyl having 1 to 4 carbon atoms and 1 to 9 halogen atoms, and additionally by phenyl, phenoxy, benzyl, benzyloxy, phenylethyl or phenylethyloxy, where each of the 6 latter substituents are optionally substituted identically or differently once to three times in the phenyl moiety by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms, or Ar represents an optionally benzo-fused heteroaryl having 2 to 9 carbon atoms and 1 to 5 identical or different heteroatoms and 1 to 5 identical or different heteroatoms, where each of these radicals is substituted once or more than once by halogen, hydroxyl, cyano, nitro, straight-chain or branched alkyl 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkylsulphonyl having 1 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, dialkylamino having 1 to 6 carbon atoms in each alkyl moiety, alkoxycarbonyl having 1 to 6 carbon atoms in the alkoxy moiety, alkoximinoalkyl having 1 to 6 carbon atoms in the alkoxy moiety and 1 to 6 carbon atoms in the alkyl moiety, doubly linked alkylene having 1 to 6 carbon atoms, which is optionally substituted identically or differently once to three times by halogen, alkyl having 1 to 4 carbon atoms-and/or halogenoalkyl having 1 to 4 carbon atoms and 1 to 9 identical or different halogen atoms, dioxyalkylene having 1 to 6 carbon atoms, which is optionally substituted identically or differently once to three times by halogen, alkyl having 1 to 4 carbon atoms and/or halogenoalkyl having 1 to 4 carbon atoms and 1 to 9 halogen atoms, cycloalkyl having 3 to 7 carbon atoms, which is optionally substituted identically or differently once to three times by halogen, alkyl having 1 to 4 carbon atoms and/or halogenoalkyl having 1 to 4 carbon atoms and 1 to 9 halogen atoms, heterocyclyl having 3 to 7 ring members, 2 to 6 carbon atoms and 1 to 3 identical or different heteroatoms wherein the heteroatoms are oxygen and/or sulphur, which is optionally substituted identically or differently once to three times by halogen, alkyl having 1 to 4 carbon atoms and/or halogenoalkyl having 1 to 4 carbon atoms and 1 to 9 halogen atoms, and additionally by phenyl, phenoxy, benzyl, benzyloxy, phenylethyl or phenylethyloxy, where each of the 6 latter substituents are optionally substituted in the phenyl moiety identically or differently once to three times by halogen, alkyl having 1 to 4 carbon atoms, alkoxy having 1 to 4 carbon atoms, halogenoalkyl having 1 to 4 carbon atoms and 1 to 9 identical or different halogen atoms and/or by halogenoalkoxy having 1 to 4 carbon atoms and 1 to 9 identical or different halogen atoms.

$R^3$ represents alkyl.

13. The compound according to claim 12, wherein the substituent on the Ar moiety is halogen, alkyl or phenoxy.

* * * * *

UNITED STATES PATENT AND TRADEMARK OFFICE
CERTIFICATE OF CORRECTION

PATENT NO. : 5,580,868
DATED : December 3, 1996
INVENTOR(S) : Lunkenheimer, et al.

It is certified that error appears in the above-indentified patent and that said Letters Patent is hereby corrected as shown below:

Col. 31, line 25    After " alkyl " insert -- having 1 to --

Signed and Sealed this

Seventeenth Day of June, 1997

Attest:

BRUCE LEHMAN

Attesting Officer     Commissioner of Patents and Trademarks